United States Patent [19]
Helsley et al.

[11] B 3,991,076
[45] Nov. 9, 1976

[54] AMINOALKYLTHIOPYRANOPYRROLES

[75] Inventors: Grover C. Helsley, Pottersville, N.J.; C. R. Taylor, Jr., Mechanicsville, Va.

[73] Assignee: American Hoechst Corporation, Bridgewater, N.J.

[22] Filed: June 7, 1974

[21] Appl. No.: 477,481

[44] Published under the second Trial Voluntary Protest Program on February 3, 1976 as document No. B 477,481.

[52] U.S. Cl. ................. 260/326.9; 260/247.1 L; 260/268 BC; 260/293.57; 260/309.7; 260/326.5 SA; 260/326.62; 424/248; 424/250; 424/267; 424/273; 424/274; 424/275

[51] Int. Cl.² ........................................ A61K 31/40
[58] Field of Search ................. 260/326.82, 326.9

[56] References Cited
UNITED STATES PATENTS
3,704,237   11/1972   Suh ............................. 260/294.8 B

*Primary Examiner*—Frederick E. Waddell
*Attorney, Agent, or Firm*—Curtis, Morris & Safford

[57] ABSTRACT

Aminoalkylthiopyranopyrroles and related compounds of the formula

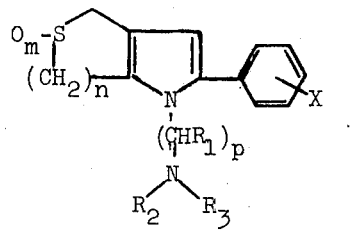

in which $R_1$, $R_2$, $R_3$, X, m, n and p are as defined below, and their physiologically tolerable acid addition salts are disclosed to possess antiinflammatory and antiarrhythmic properties. A process for their preparation is also disclosed.

8 Claims, No Drawings

AMINOALKYLTHIOPYRANOPYRROLES

This invention relates to aminoalkylthiopyranopyrroles and related compounds having antiinflammatory and antiarrythmic properties, and to process for the preparation thereof.

To the best of our knowledge, the compounds of this invention have not heretofore been described. The only reported example of a thiopyrano[4,3-b]pyrrole known to us is 1,2,3,7-tetrahydro-1-methyl-7,7-diphenyl-4-thiopyrano-[4,3-b]pyrrole-4,6-dione [Angew. Chem. Int. Ed. Engl., 6, 366 (1967)].

The compounds of the invention have the formula

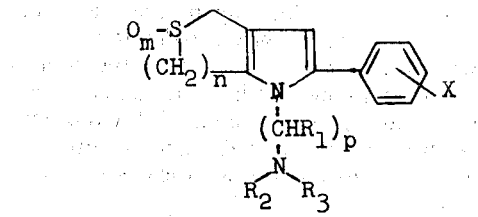

wherein X represents hydrogen, halogen, hydroxy, alkyl of 1 to 4 carbon atoms, alkoxy of 1 to 4 carbon atoms, nitro, amino, trifluoromethyl, or cyano; $m$ is an integer from 0 to 2; $n$ is 1, 2 or 3; $p$ is 2 or 3; $R_1$ and $R_2$ are hydrogen or alkyl of 1 to 4 carbon atoms; $R_3$ is alkyl of 1 to 4 carbon atoms; or $R_2$ and $R_3$ together with the nitrogen atom to which they are attached form a heterocycle selected from the group consisting of pyrrolidino, piperidino, piperazinyl, imidazolidonyl, and morpholino; and their physiologically tolerable acid addition salts. The compounds of the present invention are useful as antiinflammatory and antiarrhythmic agents.

The preferred compounds of the present invention are aminoalkylthiopyranopyrroles of the formula

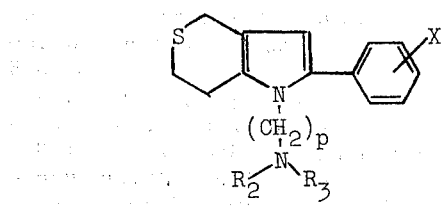

wherein X represents hydrogen, halogen, lower alkyl, lower alkoxy or trifluoromethyl; $p$ is the integer 2 or 3; $R_2$ is hydrogen or alkyl of 1 to 4 carbon atoms; $R_3$ is alkyl of 1 to 4 carbon atoms, or $R_2$ and $R_3$ together with the nitrogen atom to which they are attached form a heterocycle selected from the group consisting of pyrrolidino and piperidino; and their acid addition salts.

The compounds of the present invention are prepared by the reaction of an appropriate diketone with an appropriate aminoalkylamine as illustrated in the following equation:

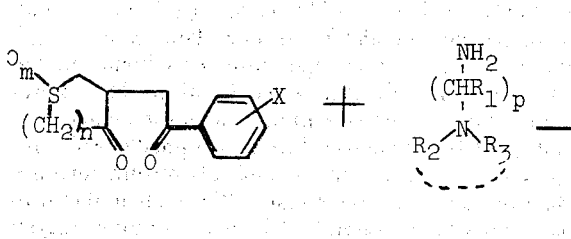

wherein X, $p$, $m$, $n$, $R_1$, $R_2$, and $R_3$ are as defined earlier.

In the preferred procedure of the invention, a substituted 3-phenacyl-2,3,5,6-tetrahydrothiopyran-4-one is reacted with an aminoalkylamine, with or without a solvent such as ethanol or acetic acid, at a temperature between 0° and 150°C for a period of time of from several minutes to 24 hours in the presence or absence of an acidic catalyst such as hydrochloric acid.

Alternatively, an aminoalkylthiopyranopyrrole or related compound can be oxidized to the sulfoxide or sulfone as illustrated in the following equations:

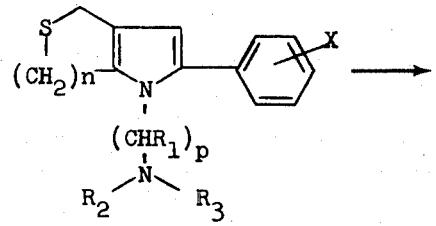

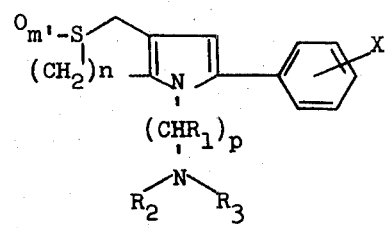

wherein $m'$ represents the integer 1 or 2, and $p$, $n$, X, $R_1$, $R_2$ and $R_3$ are as defined earlier.

The compounds of the invention are useful as antiinflammatory agents because of their ability to suppress inflammation in mammals. The activity of the compounds is demonstrated in the carrageenin-induced rat paw edema antiinflammatory assay [Proc. Soc. Expl. Biol. Med., III, 544 (1962)]. For example, at a dose of 200 mg/kg of body weight, 1-(3-dimethylaminopropyl)-2-phenyl-1,4,6,7-tetrahydrothiopyrano [4,3-b]pyrrole hydrochloride, 1-(2-dimethylaminoethyl)-2-(4-chlorophenyl)-1,4,6,7-tetrahydrothiopyrano[4,3-b]pyrrole, and 1-(1-dimethylamino-2-propyl)-2-(4-bromophenyl)-1,4,6,7-tetrahydrothiopyrano[4,3-b]pyrrole effect a 69%, 53% and 68% inhibition of edema, respectively.

The compounds of the invention are also useful as antiarrhythmic agents due to their ability to alleviate cardiac arrhythmias. The activity of the compounds is demonstrated in the isolated rabbit atrium [B. Katzung in "Selected Pharmacological Testing Methods," Volume 3, edited by A. Burger, Marcel Dekker, New York (1968), p. 198] wherein the compounds effect an increase in the functional refractory period. Compounds are dissolved in KrebsHenseleit solution, and the percent change in the functional refractory period is monitored with an oscilloscope. Thus, for example, at a concentration of $10^{-5}$ molar, 1-(2-dimethylaminoethyl)-2-(4-fluorophenyl)-1,4,6,7-tetrahydrothi-

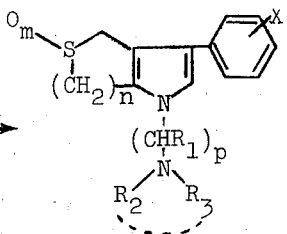

opyrano[4,3-b]pyrrole hydrochloride exhibits a 150% increase in the functional refractory period. Similarly, concentrations of $2:10^{-5}$, $10^{-5}$, $10^{-6}$, and $10^{-5}$ molar, respectively, of 1-(2-dimethylaminoethyl)-2-(3-trifluoromethylphenyl)-1,4,6,7-tetrahydrothiopyrano[4,3-b]pyrrole; 1-(3-dimethylaminopropyl)-2-(4-bromophenyl)-1,4,6,7-tetrahydrothiopyrano[4,3-b]pyrrole; 1-(3-pyrrolidinylpropyl)-2-(4-fluorophenyl)-1,4,6,7-tetrahydrothiopyrano[4,3-b]pyrrole hydrochloride; and 1-(3-dimethylaminopropyl)-2-(4-methoxyphenyl)-1,4,6,7-tetrahydrothiopyrano[4,3-b]pyrrole hydrochloride effect a 257%, 158%, 329% and 186% increase in the functional refractory period.

Examples of other compounds of the invention are:

1-(3-piperidinylpropyl)-2-(4-fluorophenyl)-1,4,6,7-tetrahydrothiopyrano[4,3-b]pyrrole 2-(3-methoxyphenyl)-1-(3-methylaminoethyl)-1,4,6,7-tetrahydrothiopyrano[4,3-b]pyrrole 1-(3-diethylaminopropyl)-4,6-dihydro-2-(3-trifluoromethylphenyl)-thieno[3,4-b]pyrrole hydrochloride 1-(3-dipropylaminopropyl)-2-phenyl-1,4,6,7-tetrahydropyrano[4,3-b]pyrrole-5,5-dioxide.

The active compounds of the invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 7% to about 70% of the weight of the unit. The amount of active compound in such compositions is such that a suitable dosage will be obtained. Preferred compositions and preparations according to the present invention are prepared so that an oral dosage unit form contains between 1 to 250 milligrams of active compound.

The tablets, pills, capsules, troches, and the like may also contain the following tablets: a binder such as hydroxypropyl cellulose, ethyl cellulose, acacia, polyvinyl pyrrolidine, cornstarch, or gelatin; an excipient such as starch, lactose, sucrose, microcrystalline cellulose, or dibasic calcium phosphate; a disintegrating agent such as alginic acid, potato starch, microcrystalline cellulose, or the like; a lubricant such as magnesium stearate, talc, stearic acid, or PEG 6000; a sweetening agent such as sucrose or saccharin; and a flavoring agent such as peppermint, methyl salicylate, or orange flavoring. When the dosage unit form is a capsule, it may also contain a liquid carrier such as a fatty acid. Other dosage unit forms may contain various materials which modify the physical form of the dosage unit, for example, as coatings. Thus, tablets or pills may be coated with sugar, shellac, or cellulose derivatives. A syrup may contain, in addition to the above compounds, sucrose as a sweetening agent, certain preservatives, dyes, colorings and flavorings. Materials used in preparing these various components must be pharmaceutically pure.

The compounds of this invention may also be intraveneously administered as sterile aqueous solutions. The pH of these solutions may be adjusted with phosphate or citrate buffers, and the solutions may contain preservatives. The solution should contain at least 0.5% of active compound and may conveniently contain from 1 to 10% of active compound. The concentration will be such that a suitable dosage will be obtained.

Acids useful for preparing the physiologically tolerable acid addition salts of the compounds of the invention include inorganic acids such as hydrochloric, hydrobromic, sulfuric, nitric, phosphoric and perchloric acids, as well as organic acids such as oxalic, tartaric, citric, acetic, succinic, maleic and ethane disulfonic acids.

The preferred routes of administering the compounds of this invention are orally and intraveneously.

EXAMPLE 1

1-(3-Dimethylaminopropyl)-2-phenyl-1,4,6,7-tetrahydrothiopyrano[4,3-b]pyrrole hydrochloride a. A solution of 103 g (0.89 mole) of tetrahydrothiopyran-4-one, 95 g (1.33 moles) of pyrrolidine, and one l. of anhydrous benzene is heated under reflux in a nitrogen atmosphere for 2 hours until the theoretical amount of water has collected in a Dean-Stark trap. The solvent is distilled, and the residue is fractionated under reduced pressure to provide 5,6-dihydro-4-(1-pyrrolidinyl)-2H-thiopyran as a colorless liquid, b.p. 124° (0.01 mm).

b. A solution of 56.3 g (0.28 mole) of phenacyl bromide in 100 ml. of dimethylformamide is added dropwise during 20 minutes under nitrogen to a cold stirred solution of 47.6 g (0.28 mole) of 5,6-dihydro-4-(1-pyrrolidinyl)-2H-thiopyran and 300 ml. of anhydrous dimethylformamide. After 2 hours, the solution is diluted with H$_2$O and extracted with chloroform. The chloroform solution is washed with water, dried over magnesium sulfate and concentrated. The product is crystalized from ethanol to give crystals of 3-phenacyl-2,3,5,6-tetrahydrothiopyran-4-one. This is recrystalized from ethanol to yield crystals; m.p. 101.5° to 103.5° C.

c. A solution of 3.0 g (0.013 mole) of 3-phenacyl-2,3,5,6-tetrahydrothiopyran-4-one, 1.33 g of 3-dimethylaminopropylamine, 20 ml. of ethanol, and one drop of concentrated hydrochloric acid is heated under reflux under nitrogen for 1.5 hours, and then cooled to ambient temperature. The reaction mixture is treated with 4 ml. of saturated ethereal hydrogen chloride and diluted to the cloud point with ether. The solid which separates is collected and recrystallized from ethanol to provide colorless crystals of 1-(3-dimethylaminopropyl)-2-phenyl-1,4,6,7-tetrahydrothiopyrano[4,3-b]pyrrole hydrochloride, m.p. 225° to 227° C. dec.

Analysis: Calc. for $C_{18}H_{25}ClN_2S$: 64.17% C; 7.48% H; 8.31% N; Found: 63.94% C; 7.51% H; 8.40% N.

EXAMPLE 2

1-(3-Dimethylaminopropyl)-2-(4-bromophenyl)-1,4,6,7-tetrahydrothiopyrano[4,3-b]pyrrole a. A suspension of 41.7 g (0.15 moles) of p-bromophenacyl bromide and 50 ml. of dimethylformamide is added dropwise under nitrogen to a cold stirred solution of 25.4 g (0.15 mole) of 5,6-dihydro-4-(1-pyrrolidinyl)-2H-thiopyran [Example 1 (a)], and 150 ml. of anhydrous dimethylformamide. The reaction mixture is stirred at room temperature for 16 hours, diluted with water, and extracted with chloroform. The chloroform solution is dried over magnesium sulfate and concentrated. The residue is chromatographed on silica gel and eluted with a benzene and chloroform mixture. The solid product is recrystallized from ethanol to provide off-white crystals of 3-(4-bromophenacyl)-2,3,5,6-tetrahydrothiopyran-4-one, m.p. 87.5° to 89.5°C.

b. A solution of 60 g (0.019 mole) of 3-(4-bromophenacyl)-2,3,5,6-tetrahydrothiopyran-4-one, 1.97 g of 3-dimethylaminopropylamine, 20 ml. of ethanol, and one drop of concentrated hydrochloric acid is heated under reflux under nitrogen for 2.5 hours and allowed to stand overnight during which time crystals precipitated. Recrystallization from ethanol gives colorless crystals of 1-(3-dimethylaminopropyl)-2-(4-bromophenyl)-1,4,6,7-tetrahydrothiopyrano[4,3-b]-pyrrole, m.p. 88° to 90°C.

Analysis: Calc. for $C_{18}H_{23}BrN_2S$: 56.99% C; 6.11% H; 7.38% N Found: 57.03% C; 6.16% H; 7.59% N.

EXAMPLE 3

2-(4-Bromophenyl)-1-(2-ethylaminoethyl)-1,4,6,7-tetrahydrothiopyrano[4,3-b]pyrrole A solution of 4.0 g (0.012 mole) of 3-(4-bromophenacyl)-2,3,5,6-tetrahydrothiopyran-4-one [Example 2 (a)], 1.3 g of ethylaminoethylamine, 14 ml. of ethanol, and one drop of concentrated hydrochloric acid is heated under reflux for 2.5 hours, cooled to −5°C, and diluted with water. The oil which separates is collected and triturated with water to provide a solid. The resultant solid is recrystallized from ethanol to give off-white crystals of 1-(2-ethylaminoethyl)-2-(4-bromophenyl)-1,4,6,7-tetrahydrothiopyrano[4,3-b]pyrrole, m.p. 84° to 85°C.

Analysis: Cal. for $C_{17}H_{21}BrN_2S$: 55.88% C; 5.79% H; 7.61% N Found: 55.93% C; 5.92% H; 7.66% N.

EXAMPLE 4

1-(1-Dimethylamino-2-propyl)-2-(4-bromophenyl)-1,4,6,7-tetrahydrothiopyrano[4,3-b]pyrrole hydrochloride a. A solution of 5.5 g (0.017 mole) of 3-(4-bromophenacyl)-2,3,5,6-tetrahydrothiopyran-4-one [Example 2 (a)], 1.6 g of 2-amino-1-dimethylaminopropane, 16 ml. of ethanol, and one drop of concentrated hydrochloric acid is heated under reflux for 3 hours, cooled to 5°C, and filtered to provide a solid product. The resulting product is dissolved in ethanol, the solution is acidified with ethereal hydrogen chloride and diluted to the cloud point with ether. Upon standing, a solid separates. Recrystallization from ethanol gives off-white crystals of 1-(1-dimethylamino-2-propyl)-2-(4-bromophenyl)-1,4,6,7-tetrahydrothiopyrano[4,3-b]pyrrole hydrochloride, m.p. 237° to 238°C. dec.

Analysis: Calc. for $C_{18}H_{24}BrClN_2S$: 51.99% C; 5.82% H; 6.74% N Found: 51.50% C; 5.96% H; 6.55% N.

EXAMPLE 5

1-(2-Dimethylaminoethyl)-2-(4-fluorophenyl)-1,4,6,7-tetrahydrothiopyrano[4,3-b]pyrrole hydrochloride a. A solution of 21.7 g (0.10 mole) of 4-fluorophenacyl bromide in 50 ml. of dimethylformamide is added dropwise to a cold stirred solution of 16.9 g (0.10 mole) of 5,6-dihydro-4-(1-pyrrolidinyl)-2H-thiopyran [Example 1 (a)], and 100 ml. of dimethylformamide under nitrogen. After 6 hours at ambient temperature, the mixture is diluted with water and extracted with chloroform. The chloroform solution is washed with water, dried over magnesium sulfate and concentrated to an oil. Crystallization and recrystallization from ethanol gives off-white crystals of 3-(4-fluorophenacyl)-2,3,5,6-tetrahydrothiopyran-4-one, m.p. 111.5° to 113.5°C.

b. A solution of 4.02 g of (0.016 mole) of 3-(4-fluorophenacyl)-2,3,5,6-tetrahydrothiopyran-4-one, 1.54 g of dimethylaminoethylamine, 50 ml. of ethanol, and 2 drops of concentrated hydrochloric acid is heated under reflux for 1.5 hours and cooled to ambient temperature. 4 mls. of saturated ethanolic hydrogen chloride are added to effect precipitation of crystals. Recrystallization from ethanol gives colorless crystals of 1-(2-dimethylaminoethyl)-2-(4-fluorophenyl)-1,4,6,7-tetrahydrothiopyran[4,3-b]pyrrole hydrochloride, m.p. 238.5° to 240°C. dec.

Analysis; Calc. for $C_{17}H_{22}ClN_2S$: 59.90% C; 6.51% H; 8.22% N Found: 59.83% C; 6.52% H; 8.20% N.

EXAMPLE 6

1-(3-Dimethylaminopropyl)-2-(4-fluorophenyl)-1,4,6,7-tetrahydrothiopyrano[4,3-b]pyrrole hydrochloride A solution of 4.0 g (0.016 mole) of 3-(4-fluorophenacyl)-2,3,5,6-tetrahydrothiopyran-4-one [Example 5 (a)], 1.62 g of 3-dimethylaminopropylamine and 40 ml. of ethanol is heated under reflux for 2.5 hours, cooled, treated with 4 ml. of saturated ethereal hydrogen chloride, warmed to boiling, and diluted to the cloud point with ether. Upon cooling a solid separates. Recrystallization from ethanol gives off-white crystals of 1-(3-dimethylaminopropyl)-2-(4-fluorophenyl)-1,4,6,7-tetrahydrothiopyrano[4,3-b]pyrrole hydrochloride, m.p. 199° to 201°C. dec.

Analysis: Calc. for $C_{18}H_{24}ClFN_2S$: 60.92% C; 6.82% H; 7.89% N Found: 60.89% C; 6.87% H; 8.03% N.

EXAMPLE 7

1-(3-Pyrrolidinylpropyl)-2-(4-fluorophenyl)-1,4,6,7-tetrahydrothiopyrano[4,3-b]pyrrole hydrochloride A solution of 1.0 g (0.04 mole) of 3-(4-fluorophenacyl)-2,3,5,6-tetrahydrothiopyran-4-one [Example 5 (a)], 0.51 g of 3-pyrrolidinylpropylamine, and 5 ml. of ethanol is heated under reflux under nitrogen for 25 hours and concentrated to an oil which is chromatographed on silca gel. Eluted with a benzene-methanol mixture is an oil which is dissolved in ethanol. The ethanolic solution is treated with saturated ethereal hydrogen chloride and diluted to the cloud point with ether to effect the precipitation of a solid. The solid is recrystallized from ethanol to give off-white crystals of 1-(3-pyrrolidinylpropyl)-2-(4-fluorophenyl)-1,4,6,7-tetrahydrothiopyrano[4,3-b]pyrrole hydrochloride, m.p. 214.5° to 217°C. dec.

Analysis: Calc. for $C_{20}H_{26}ClFN_2S$: 63.06% C; 6.88% H; 7.35% N Found: 62.95% C; 6.88% H; 7.39% N.

EXAMPLE 8

1-(3-Dimethylaminopropyl)-2-(4-methoxyphenyl)1,4,6,7-tetrahydrothiopyrano[4,3-b]pyrrole hydrochloride a. A solution of 23.7 g (0.10 mole) of p-methoxyphenacyl bromide in 50 ml. of dimethylformamide is added dropwise under nitrogen to a cold stirred solution of 16.9 g (0.10 mole) of 5,6-dihydro-4-(1-pyrrolidinyl)-2H-thiopyran [Example 1 (a)] and 10 ml. of dimethylformamide. After 5 hours the reaction mixture is diluted with water and extracted with chloroform. The chloroform solution is washed with water, dried over magnesium sulfate, and concentrated to an oil which solidifies. The solid is suspended in methanol. The mixture is filtered and the filtrate is concentrated to a solid. The resulting solid is recrystallized from methanol and then from acetic acid to give off-white crystals of 3-(4-methoxyphenacyl)-2,3,5,6-tetrahydrothiopyran-4-one, m.p. 123° to 125°C.

b. A solution of 3.09 g (0.012 mole) of 3-(4-methoxyphenacyl)-2,3,5,6-tetrahydrothiopyran-4-one, 1.22 g of dimethylaminopropylamine, 20 ml. of ethanol and one drop of concentrated hydrochloric acid is heated under reflux for 1.5 hours, cooled to ambient temperature, treated with 4 ml. of saturated ethereal hydrogen chloride, and diluted to the cloud point with ether. A brown solid precipitates. The solid is recrystallized from 2-propanol to give tan crystals of 1-(3-dimethylaminopropyl)-2-(4-methoxyphenyl)-1,4,6,7-tetrahydrothiopyrano[4,3-b]pyrrole hydrochloride, m.p. 193 to 194°C.

Analysis: Calc. for $C_{19}H_{27}ClN_2OS$: 62.19% C; 7.42% H; 7.63% N Found: 61.74% C; 7.53% H: 7.84% N.

EXAMPLE 9

2-(4-Chlorophenyl)-1-(2-dimethylaminoethyl)-1,4,6,7-tetrahydrothiopyrano[4,3-b]pyrrole a. A solution of 23.4 g (0.10 mole) of p-chlorophenacyl bromide in 50 ml. of dimethylformamide is added dropwise under nitrogen to a stirred solution of 16.9 g (0.10 mole) of 5,6-dihydro-4-(1-pyrrolidinyl)-2H-thiopyran [Example 1 (a)] and 100 ml. of dimethylformamide. After 6 hours at ambient temperature the mixture is diluted with water and extracted with chloroform. The chloroform solution is washed with water, dried over magnesium sulfate and concentrated to an oil. The oil is chromatographed on silica gel and eluted with benzene and chloroform mixtures to give an oil which solidifies. The resulting solid is recrystallized from ethanol to give off-white crystals of 3-(4-chlorophenacyl)-2,3,5,6-tetrahydrothiopyran-4-one, m.p. 78° to 81°C.

b. A solution of 5.0 g (0.019 mole) of 3-(4-chlorophenacyl)-2,3,5,6-tetrahydrothiopyran-4-one, 7.14 g of dimethylaminoethylamine and 15 ml. of acetic acid is heated under reflux under nitrogen for 24 hours, diluted with water, acidified with hydrochloric acid, extracted with ether, neutralized with sodium hydroxide, and extracted with chloroform. The chloroform solution is dried over magnesium sulfate and concentrated. The residue is recrystallized from ethanol to give off-white crystals of 1-(2-dimethylaminoethyl)-2(4-chlorophenyl)-1,4,6,7-tetrahydrothiopyrano[4,3-b]pyrrole, m.p. 91.5° to 92.5°C.

Analysis: Calc. for $C_{17}H_{21}ClN_2S$: 63.63% C; 6.60% H; 8.73% N Found: 63.73% C; 6.68% H; 8.93% N.

EXAMPLE 10

1-(2-Dimethylaminoethyl)-2-(3-trifluoromethylphenyl)-1,4,6,7-tetrahydrothiopyrano[4,3-b]pyrrole a. A solution of 32.6 g of m-trifluoromethylphenacyl bromide in 10 ml. of dimethylformamide is added dropwise to a stirred solution of 20 g (0.12 mole of 5,6-dihydro-4-(1-pyrrolidinyl)-2H-thiopyran [Example 1 (a)] and 100 ml. of dimethylformamide. After 2 hours, the mixture is diluted with water and extracted with chloroform. The chloroform solution is washed with water, dried over magnesium sulfate, and concentrated to an oil. The oil is chromatographed on silica gel with benzene and chloroform mixtures to give 2,3,5,6-tetrahydro-3-(3-trifluoromethylphenacyl)thiopyran-4-one as an oil. Infrared and nuclear magnetic resonance spectra are consistent with the assigned structure.

b. A solution of 5.5 g (0.018 mole) of 2,3,5,6-tetrahydro-3-(3-trifluoromethylphenacyl)thiopyran-4-one, 1.6 g of dimethylaminoethylamine and 15 ml. of acetic acid is heated under reflux for 12 hours. The reaction solution is then diluted with water, acidified with hydrochloric acid, extracted with ether, neutralized with sodium hydroxide, and extracted with chloroform. The chloroform solution is dried over magnesium sulfate and concentrated. The residue is recrystallized from 2-propanol to give colorless crystals of 1-(2-dimethylaminoethyl)2-(3-trifluoromethylphenyl)-1,4,6,7-tetrahydrothiopyrano[4,3,-b]pyrrole, m.p. 88.5° to 90°C.

Analysis: Calc. for $C_{18}H_{21}F_3N_2S$: 61.00% C; 5.97% H; 7.90% N Found: 60.87% C; 5.97% H; 7.91% N.

EXAMPLE 11

1-(3-Dimethylaminopropyl)-2-phenyl-1,4,6,7-tetrahydrothiopyrano[4,3-b]pyrrole-5,5-dioxide a. A mixture of 18.0 g (0.12 mole) of tetrahydrothiopyran-4-one-1,1-dioxide, 13.0 g (0.18 mole) of pyrrolidine, 50 g of 5A molecular sieves and 400 ml. of anhydrous benzene is shaken for 3.5 hours and filtered. The filtrate is concentrated under reduced pressure to 5,6-dihydro-4-(1-pyrrolidinyl)-2H-thiopyran-1,1-dioxide as a gummy solid.

b. 22.8 g (0.11 mole) of phenacyl bromide are added dropwise to a cold stirred solution of 23.0 g (0.11 mole) of 5,6-dihydro-4-(1-pyrrolidinyl)-2H-thiopyran-1,1-dioxide and 100 ml. of dimethylformamide. The mixture is stirred for 18 hours, diluted with water, and extracted with chloroform. The chloroform solution is dried over magnesium sulfate and concentrated to a solid. Chromatography on silica gel with a benzene and methanol mixture followed by recrystallization from methanol gives colorless crystals of 2-phenacyl-2,3,5,6-tetrahydrothiopyran-4-one-1,1-dioxide, m.p. 157.5° to 159°C.

c. A solution of 2.0 g (0.0075 mole) of 3-phenacyl-2,3,5,6-tetrahydrothiopyran-4-one-1,1-dioxide, 0.85 g of dimethylaminopropylamine and 30 ml. of acetic acid is heated under reflux for 5 hours. The reaction solution is cooled, diluted with water, adjusted to a pH of 1 with hydrochloric acid, and then washed with ether. The solution is made basic with sodium bicarbonate and extracted with ether. The ether extract is dried and concentrated to a solid. The solid is recrystallized from 2-propanol to give off-white needles of 1-(3-dimethylaminopropyl)-2-phenyl-1,4,6,7-tetrahydrothiopyrano[4,3-b]pyrrole-5,5-dioxide, m.p. 123° to 125°C.

Analysis; Calc. for $C_{18}H_{24}N_2O_2S$: 65.03% C; 7.28% H; 8.43% N Found: 64.68% C; 7.28% H; 8.39% N.

We claim:

1. A compound of the formula

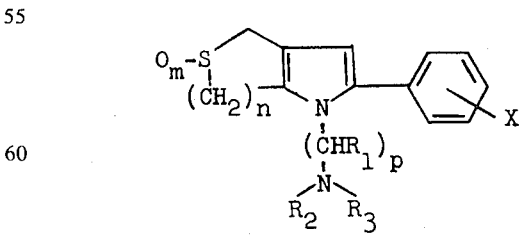

wherein X is hydrogen, halogen, hydroxy, lower alkyl, lower alkoxy, nitro, amino, trifluoromethyl or cyano; $m$ is an integer from 0 to 2; $n$ is 1, 2 or 3; $p$ is 2 or 3; $R_1$ and $R_2$ are hydrogen or alkyl of 1 to 4 carbon atoms; and $R_3$ is alkyl of 1 to 4 carbon atoms; and the physiologically tolerable acid addition salts thereof.

2. A compound as defined in claim 1 wherein X is hydrogen, halogen, alkoxy of from 1 to 2 carbon atoms or trifluoromethyl; $m$ is zero; $n$ is 2; $p$ is 2 or 3; $R_1$ is hydrogen or alkyl of 1 to 4 carbon atoms; $R_2$ is hydrogen or alkyl of 1 to 3 carbon atoms; $R_3$ is alkyl of 1 to 3 carbon atoms; and the physiologically tolerable acid addition salts thereof.

3. The compound as defined in claim 2 which is 1-(3-dimethylaminopropyl)-2-(4-bromophenyl)-1,4,6,7-tetrahydrothiopyrano[4,3-b]pyrrole.

4. The compound as defined in claim 2 which is 1-(3-dimethylaminopropyl)-2-phenyl-1,4,6,7-tetrahydrothiopyrano[4,3-b]pyrrole hydrochloride.

5. The compound as defined in claim 2 which is 1-(2-dimethylaminoethyl)-2-(3-trifluoromethylphenyl)-1,4,6,7-tetrahydrothiopyrano[4,3-b]pyrrole.

6. The compound as defined in claim 2 which is 1-(3-dimethylaminopropyl)-2-(4-methoxyphenyl)-1,4,6,7-tetrahydrothiopyrano[4,3-b]pyrrole hydrochloride.

7. The compound as defined in claim 1 which is 1-(3-dimethylaminopropyl)-2-phenyl-1,4,6,7-tetrahydrothiopyrano[4,3-b]pyrrole-5,5-dioxide.

8. A process for the preparation of the compounds defined in claim 1 which comprises reacting a γ-diketone of the formula

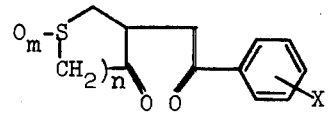

wherein X, $m$ and $n$ are as defined in claim 1 with an aminoalkylamine of the formula

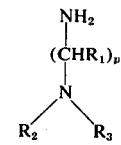

wherein $R_1$, $R_2$, $R_3$ and $p$ are as defined in claim 1.

* * * * *